US011399815B2

(12) United States Patent
Yassinzadeh et al.

(10) Patent No.: US 11,399,815 B2
(45) Date of Patent: *Aug. 2, 2022

(54) VASCULAR CLOSURE DEVICES AND METHODS PROVIDING HEMOSTATIC ENHANCEMENT

(71) Applicant: Cardiva Medical, Inc., Santa Clara, CA (US)

(72) Inventors: Zia Yassinzadeh, San Jose, CA (US); Jeffrey I. Weitz, Ancaster (CA); Alan Stafford, Hamilton (CA)

( * ) Notice: Subject to any disclaimer, the term of this patent is extended or adjusted under 35 U.S.C. 154(b) by 382 days.

This patent is subject to a terminal disclaimer.

(21) Appl. No.: 16/436,204

(22) Filed: Jun. 10, 2019

(65) Prior Publication Data
US 2019/0388076 A1 Dec. 26, 2019

Related U.S. Application Data

(63) Continuation of application No. 15/424,119, filed on Feb. 3, 2017, now Pat. No. 10,363,021, which is a (Continued)

(51) Int. Cl.
*A61B 17/00* (2006.01)
*A61B 17/34* (2006.01)
*A61B 90/00* (2016.01)

(52) U.S. Cl.
CPC .... *A61B 17/0057* (2013.01); *A61B 17/00491* (2013.01); *A61B 2017/00659* (2013.01); (Continued)

(58) Field of Classification Search
CPC .......... A61B 17/0057; A61B 17/00491; A61B 2090/032; A61B 2017/00659; (Continued)

(56) References Cited

U.S. PATENT DOCUMENTS

| 4,744,364 A | 5/1988 | Kensey et al. |
| 4,852,568 A | 8/1989 | Kensey |

(Continued)

FOREIGN PATENT DOCUMENTS

| WO | WO-9222252 A1 | 12/1992 |
| WO | WO-9505121 A1 | 2/1995 |

(Continued)

OTHER PUBLICATIONS

European search report and search opinion dated Apr. 3, 2013 for EP Application No. 06850411.

(Continued)

*Primary Examiner* — Jing Rui Ou
(74) *Attorney, Agent, or Firm* — Sunstein LLP

(57) ABSTRACT

Vascular closure devices and methods for closing a blood vessel puncture site disposed at a distal end of a tissue tract are described. A combination of the body's own natural mechanism with chemical and/or biological agents is relied upon to accelerate the hemostatic process. Included are steps of introducing a closure device through the tissue tract and deploying an expansible member at a distal end of the device within the blood vessel to occlude the puncture site. A sealing member disposed proximal the expansible member is then displaced by retracting and tensioning a coil spring so as to expose a chemical and/or biological region or release region of the device. The retraction and tensioning of the coil spring is limited by a coupling member. Exposure of blood and tissue to the chemical and/or biological sealing member promotes the clotting processing to accelerate the occlusion process in the tract.

6 Claims, 9 Drawing Sheets

Related U.S. Application Data continuation of application No. 14/849,228, filed on Sep. 9, 2015, now Pat. No. 9,597,066, which is a continuation of application No. 11/772,718, filed on Jul. 2, 2007, now Pat. No. 9,179,897, which is a continuation-in-part of application No. 11/302,951, filed on Dec. 13, 2005, now Pat. No. 7,691,127.

(52) U.S. Cl.
CPC ............ *A61B 2017/00676* (2013.01); *A61B 2017/00778* (2013.01); *A61B 2017/00884* (2013.01); *A61B 2017/00889* (2013.01); *A61B 2017/00893* (2013.01); *A61B 2017/3484* (2013.01); *A61B 2090/032* (2016.02)

(58) Field of Classification Search
CPC  A61B 2017/00676; A61B 2017/00778; A61B 2017/00884; A61B 2017/00889; A61B 2017/00893; A61B 2017/3484
See application file for complete search history.

(56) References Cited

U.S. PATENT DOCUMENTS

| | | |
|---|---|---|
| 4,890,612 A | 1/1990 | Kensey |
| 4,895,168 A | 1/1990 | Machek |
| 5,061,274 A | 10/1991 | Kensey |
| 5,108,420 A | 4/1992 | Marks |
| 5,108,421 A | 4/1992 | Fowler |
| 5,129,882 A | 7/1992 | Weldon et al. |
| 5,171,259 A | 12/1992 | Inoue |
| 5,197,971 A | 3/1993 | Bonutti |
| 5,222,974 A | 6/1993 | Kensey et al. |
| 5,258,000 A | 11/1993 | Gianturco |
| 5,290,552 A | 3/1994 | Sierra et al. |
| 5,292,332 A | 3/1994 | Lee |
| 5,383,896 A | 1/1995 | Gershony et al. |
| 5,419,765 A | 5/1995 | Weldon et al. |
| 5,454,833 A | 10/1995 | Boussignac et al. |
| 5,456,667 A | 10/1995 | Ham et al. |
| 5,456,689 A | 10/1995 | Kresch et al. |
| 5,486,195 A | 1/1996 | Myers et al. |
| 5,507,744 A | 4/1996 | Tay et al. |
| 5,540,715 A | 7/1996 | Katsaros et al. |
| 5,545,178 A | 8/1996 | Kensey et al. |
| 5,549,633 A | 8/1996 | Evans et al. |
| 5,626,601 A | 5/1997 | Gershony et al. |
| 5,630,833 A | 5/1997 | Katsaros et al. |
| 5,634,936 A | 6/1997 | Linden et al. |
| 5,649,959 A | 7/1997 | Hannam et al. |
| 5,653,730 A | 8/1997 | Hammerslag |
| 5,725,551 A | 3/1998 | Myers et al. |
| 5,728,133 A | 3/1998 | Kontos et al. |
| 5,728,134 A | 3/1998 | Barak |
| 5,782,860 A | 7/1998 | Epstein et al. |
| 5,810,810 A | 9/1998 | Tay et al. |
| 5,836,913 A | 11/1998 | Orth et al. |
| 5,851,210 A | 12/1998 | Torossian |
| 5,861,003 A | 1/1999 | Latson et al. |
| 5,868,778 A | 2/1999 | Gershony et al. |
| 5,895,398 A | 4/1999 | Wensel et al. |
| 5,922,009 A | 7/1999 | Epstein et al. |
| 5,935,147 A | 8/1999 | Kensey et al. |
| 5,951,583 A | 9/1999 | Jensen et al. |
| 5,951,589 A | 9/1999 | Epstein et al. |
| 5,957,952 A | 9/1999 | Gershony et al. |
| 5,979,453 A | 11/1999 | Savage et al. |
| 6,007,563 A | 12/1999 | Nash et al. |
| 6,012,457 A | 1/2000 | Lesh |
| 6,017,359 A | 1/2000 | Gershony et al. |
| 6,022,361 A | 2/2000 | Epstein et al. |
| 6,045,569 A | 4/2000 | Kensey et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,071,300 A | 6/2000 | Brenneman et al. |
| 6,080,182 A | 6/2000 | Shaw et al. |
| 6,126,675 A | 10/2000 | Shchervinsky et al. |
| 6,146,396 A | 11/2000 | Konya et al. |
| 6,162,240 A | 12/2000 | Cates et al. |
| 6,193,670 B1 | 2/2001 | Van et al. |
| 6,248,124 B1 | 6/2001 | Pedros et al. |
| 6,296,657 B1 | 10/2001 | Brucker |
| 6,464,712 B1 | 10/2002 | Epstein et al. |
| 6,569,185 B2 | 5/2003 | Ungs |
| 6,610,026 B2 | 8/2003 | Cragg et al. |
| 6,656,207 B2 | 12/2003 | Epstein et al. |
| 6,699,261 B1 | 3/2004 | Cates et al. |
| 6,743,195 B2 | 6/2004 | Zucker |
| 6,764,467 B1 | 7/2004 | Roby et al. |
| 6,780,197 B2 | 8/2004 | Roe et al. |
| 6,814,743 B2 | 11/2004 | Chin et al. |
| 6,818,008 B1 | 11/2004 | Cates et al. |
| 6,913,614 B2 | 7/2005 | Marino et al. |
| 6,989,022 B2 | 1/2006 | Nowakowski |
| 6,994,686 B2 | 2/2006 | Cruise et al. |
| 7,008,441 B2 | 3/2006 | Zucker |
| 7,025,776 B1 | 4/2006 | Houser et al. |
| 7,115,127 B2 | 10/2006 | Lindenbaum et al. |
| 7,223,266 B2 | 5/2007 | Lindenbaum et al. |
| 7,316,704 B2 | 1/2008 | Bagaoisan et al. |
| 7,322,976 B2 | 1/2008 | Yassinzadeh |
| 7,335,220 B2 | 2/2008 | Khosravi et al. |
| 7,572,274 B2 | 8/2009 | Yassinzadeh |
| 7,618,438 B2 | 11/2009 | White et al. |
| 7,691,127 B2 | 4/2010 | Yassinzadeh et al. |
| 7,993,366 B2 | 8/2011 | Yassinzadeh et al. |
| 8,323,305 B2 | 12/2012 | Epstein et al. |
| 8,747,435 B2 | 6/2014 | Yassinzadeh |
| 9,017,374 B2 | 4/2015 | Yassinzadeh |
| 9,179,897 B2 | 11/2015 | Yassinzadeh et al. |
| 9,597,066 B2 | 3/2017 | Yassinzadeh et al. |
| 10,363,021 B2 | 7/2019 | Yassinzadeh et al. |
| 2002/0026215 A1 | 2/2002 | Redmond et al. |
| 2002/0072767 A1 | 6/2002 | Zhu et al. |
| 2002/0133123 A1 | 9/2002 | Zucker |
| 2002/0133193 A1 | 9/2002 | Ginn et al. |
| 2003/0018357 A1 | 1/2003 | Luthra et al. |
| 2003/0045835 A1 | 3/2003 | Anderson et al. |
| 2003/0051735 A1 | 3/2003 | Pavcnik et al. |
| 2003/0055454 A1 | 3/2003 | Zucker |
| 2003/0100921 A1 | 5/2003 | Addis et al. |
| 2003/0120291 A1* | 6/2003 | Chin ............... A61B 17/32053 606/153 |
| 2003/0163146 A1 | 8/2003 | Epstein et al. |
| 2003/0191493 A1 | 10/2003 | Epstein et al. |
| 2004/0172060 A1 | 9/2004 | Cates et al. |
| 2004/0176758 A1 | 9/2004 | Yassinzadeh |
| 2004/0176798 A1 | 9/2004 | Epstein et al. |
| 2004/0243052 A1 | 12/2004 | Kauphusman et al. |
| 2004/0249342 A1 | 12/2004 | Khosravi et al. |
| 2005/0065549 A1 | 3/2005 | Cates et al. |
| 2005/0090860 A1 | 4/2005 | Paprocki |
| 2005/0107781 A1 | 5/2005 | Ostrovsky et al. |
| 2005/0216054 A1 | 9/2005 | Widomski et al. |
| 2005/0228443 A1 | 10/2005 | Yassinzadeh |
| 2005/0228444 A1 | 10/2005 | Wendlandt |
| 2005/0267522 A1 | 12/2005 | Yassinzadeh et al. |
| 2005/0277980 A1 | 12/2005 | Yassinzadeh |
| 2006/0034935 A1 | 2/2006 | Pronovost et al. |
| 2006/0189972 A1 | 8/2006 | Grossman |
| 2006/0229670 A1 | 10/2006 | Bates |
| 2007/0032823 A1 | 2/2007 | Tegg |
| 2007/0038244 A1 | 2/2007 | Morris et al. |
| 2007/0249939 A1 | 10/2007 | Gerbi et al. |
| 2010/0145383 A1 | 6/2010 | Yassinzadeh |

FOREIGN PATENT DOCUMENTS

| | | |
|---|---|---|
| WO | WO-9624290 A1 | 8/1996 |
| WO | WO-9834546 A1 | 8/1998 |

(56) References Cited

FOREIGN PATENT DOCUMENTS

| WO | WO-9840017 A2 | 9/1998 |
|---|---|---|
| WO | WO-9840017 A3 | 10/1998 |
| WO | WO-0006029 A1 | 2/2000 |
| WO | WO-0006031 A1 | 2/2000 |
| WO | WO-2007089364 A2 | 8/2007 |
| WO | WO-2007089364 A3 | 6/2008 |
| WO | WO-2009006482 A1 | 1/2009 |

OTHER PUBLICATIONS

European search report and search opinion dated Jul. 5, 2013 for EP Application No. 08772314.4.
International search report and written opinion dated Mar. 3, 2008 for PCT/US2006/061119.
International search report and written opinion dated Oct. 2, 2008 for PCT/US2008/068933.
Notice of allowance dated Jan. 28, 2010 for U.S. Appl. No. 11/302,951.
Notice of allowance dated Apr. 21, 2014 for U.S. Appl. No. 12/711,132.
Notice of allowance dated Aug. 27, 2015 for U.S. Appl. No. 11/772,718.
Notice of allowance dated Nov. 10, 2016 for U.S. Appl. No. 14/849,228.
Office action dated Feb. 13, 2009 for U.S. Appl. No. 11/302,951.
Office action dated Feb. 27, 2013 for U.S. Appl. No. 12/711,132.
Office action dated Mar. 2, 2012 for U.S. Appl. No. 12/711,132.
Office action dated Apr. 15, 2011 for U.S. Appl. No. 11/772,718.
Office action dated Jun. 22, 2009 for U.S. Appl. No. 11/772,718.
Office action dated Jul. 16, 2008 for U.S. Appl. No. 11/302,951.
Office action dated Aug. 3, 2009 for U.S. Appl. No. 11/302,951.
Office action dated Oct. 8, 2013 for U.S. Appl. No. 12/711,132.
Office action dated Oct. 12, 2012 for U.S. Appl. No. 12/711,132.
Office action dated Oct. 26, 2010 for U.S. Appl. No. 11/772,718.
Office action dated Nov. 12, 2009 for U.S. Appl. No. 11/772,718.

\* cited by examiner

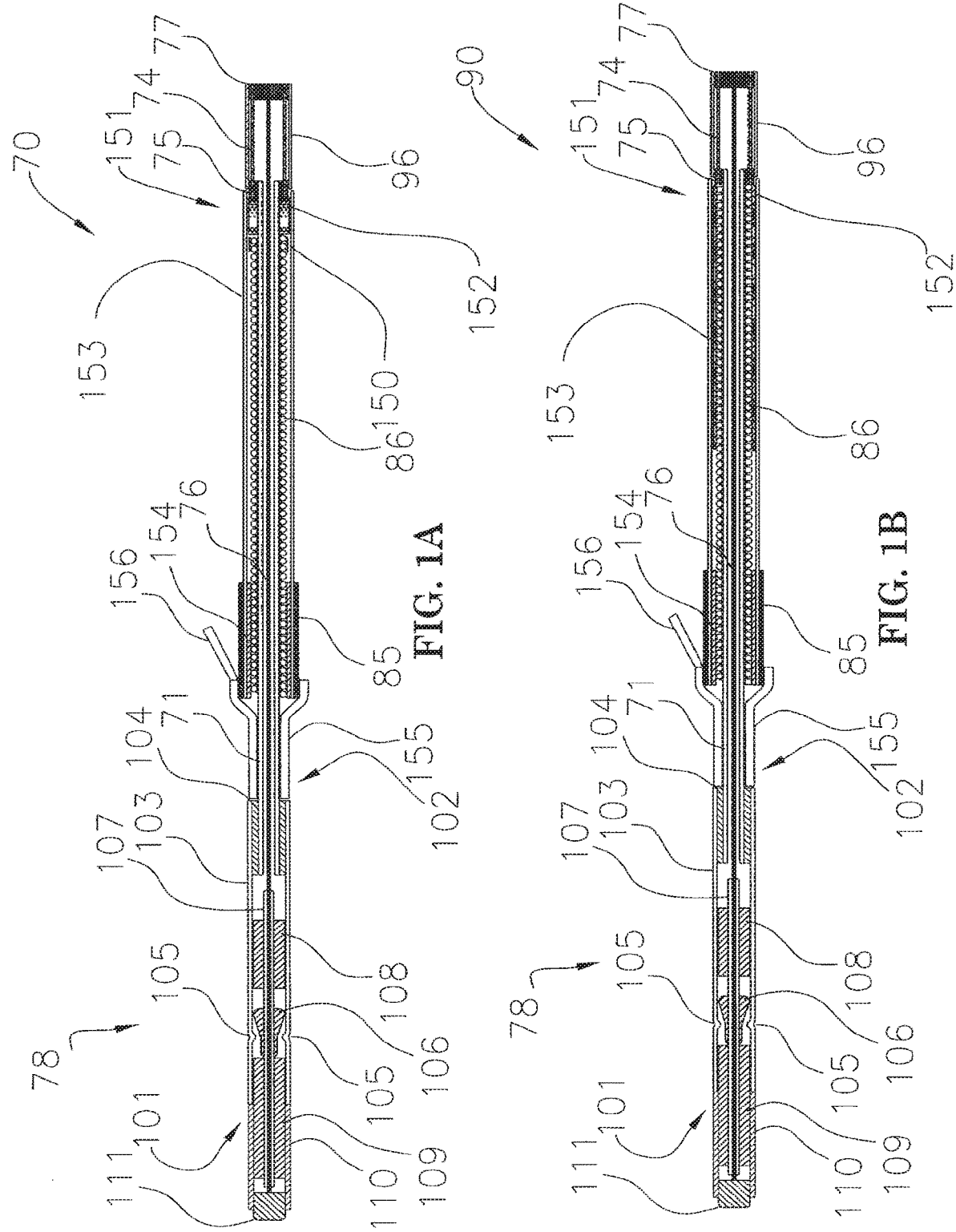

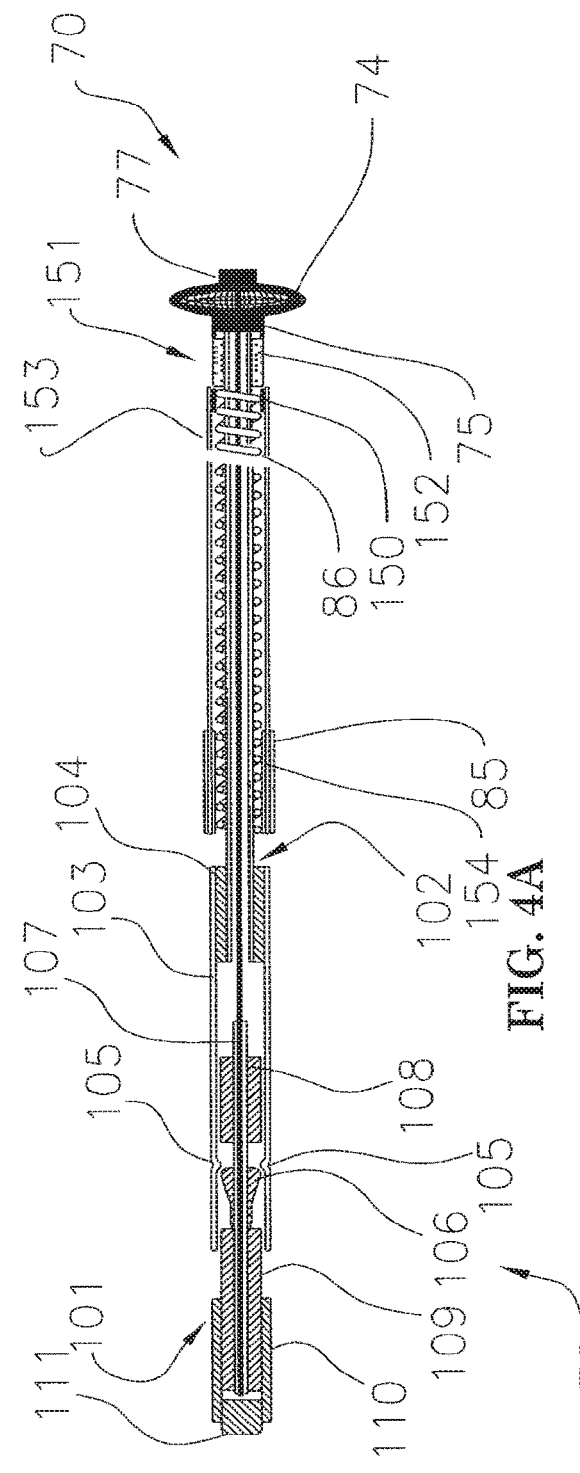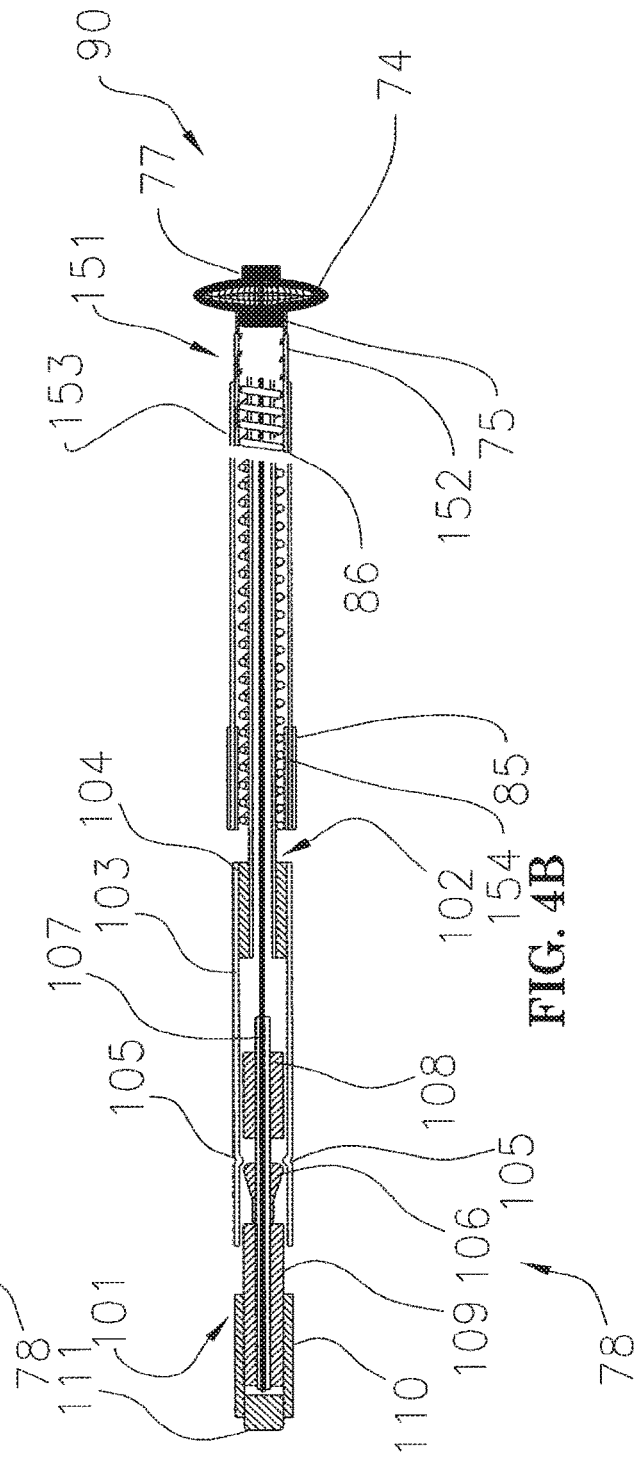

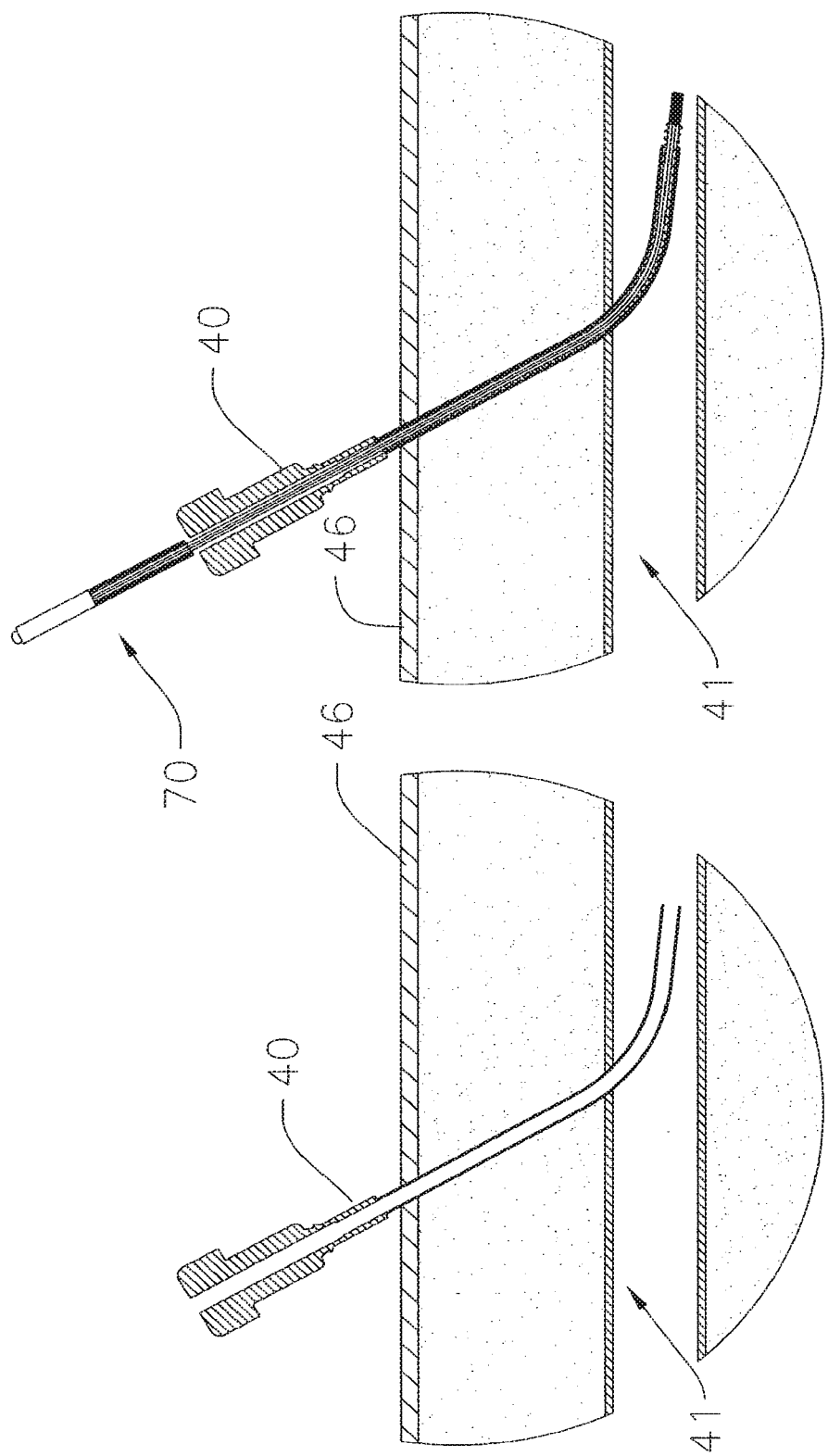

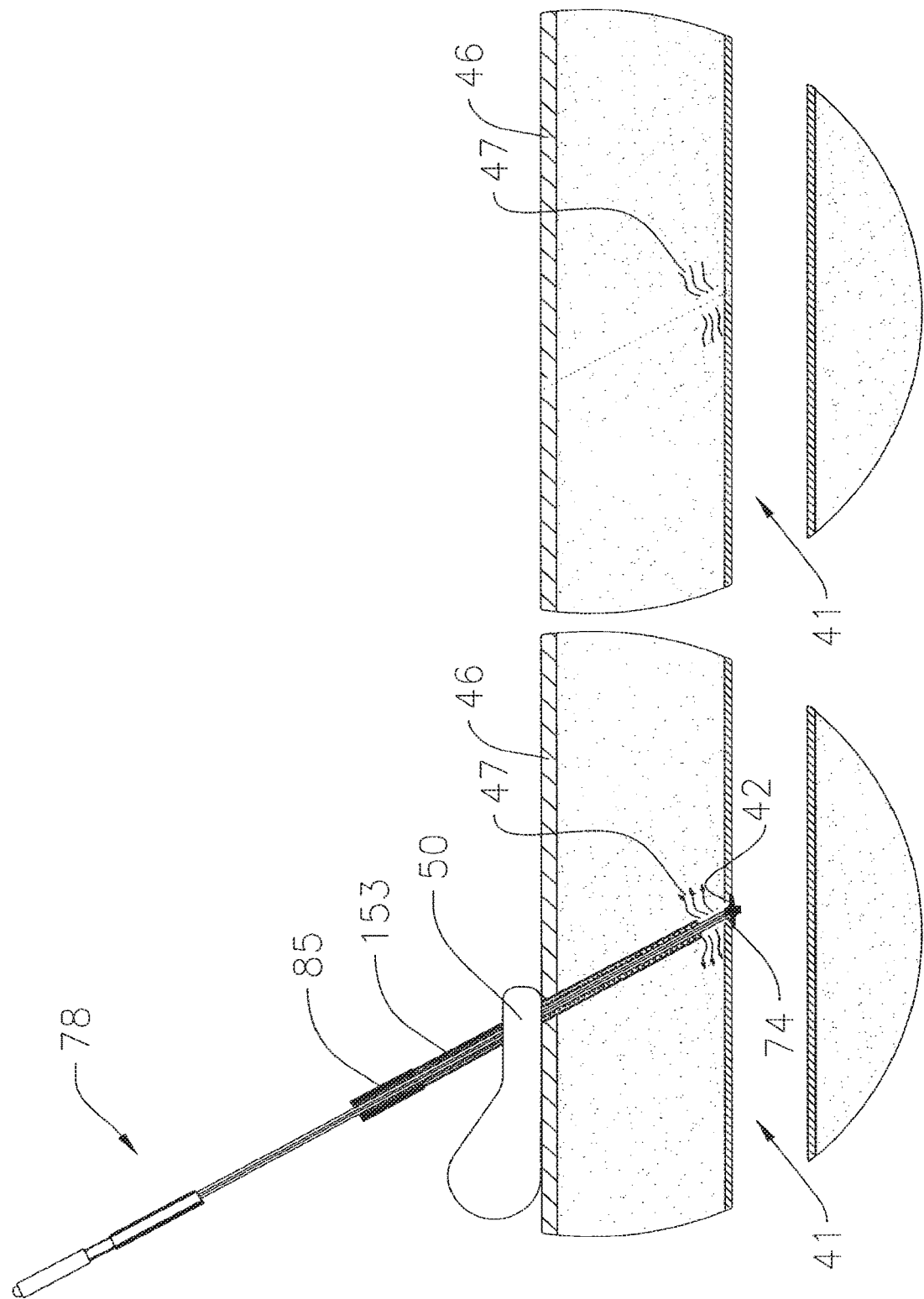

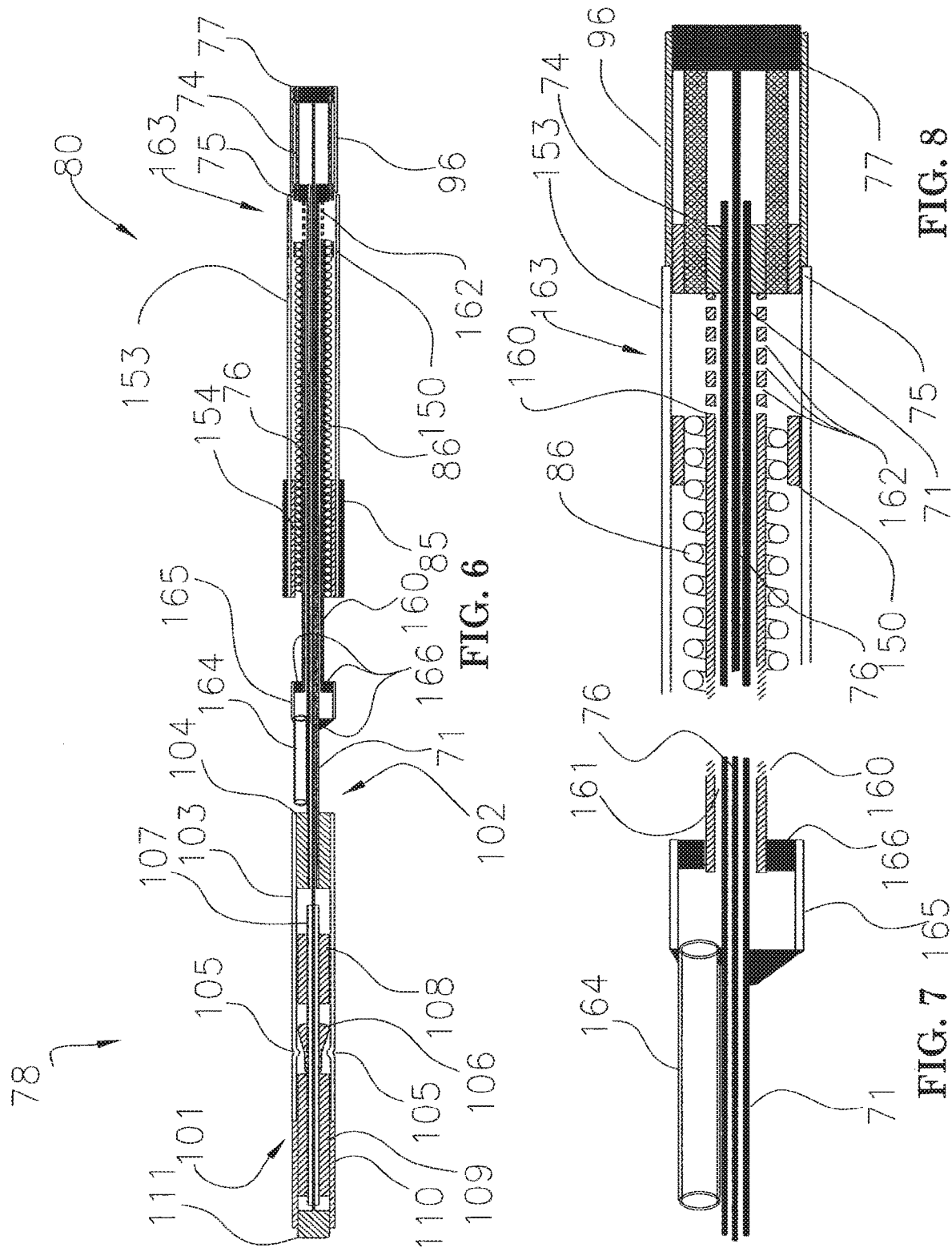

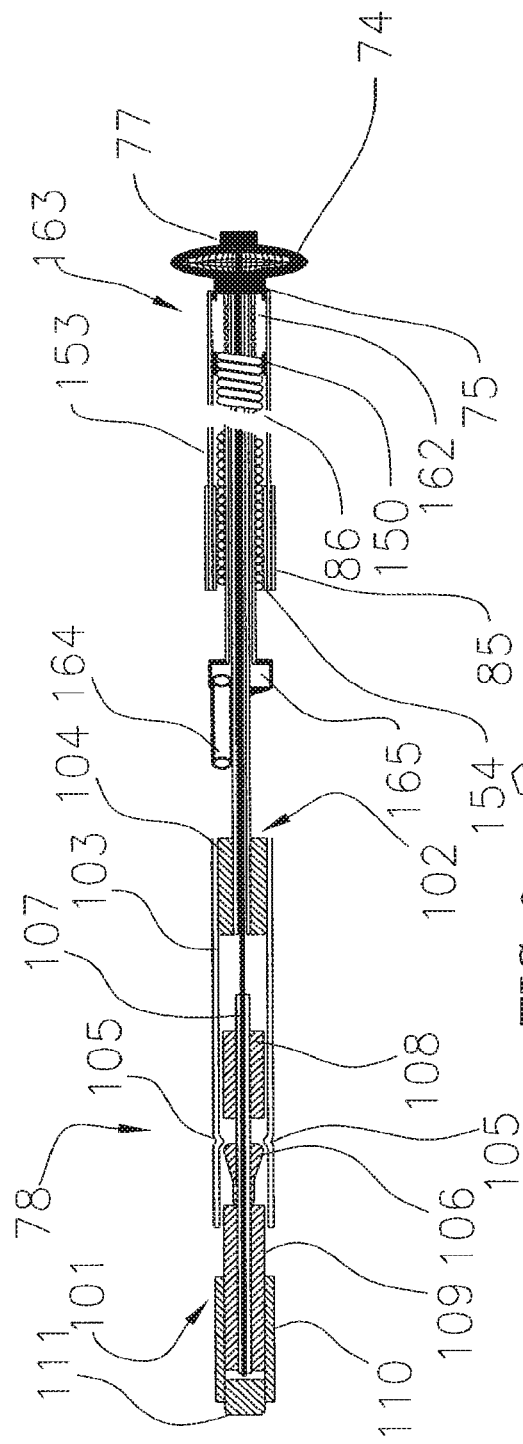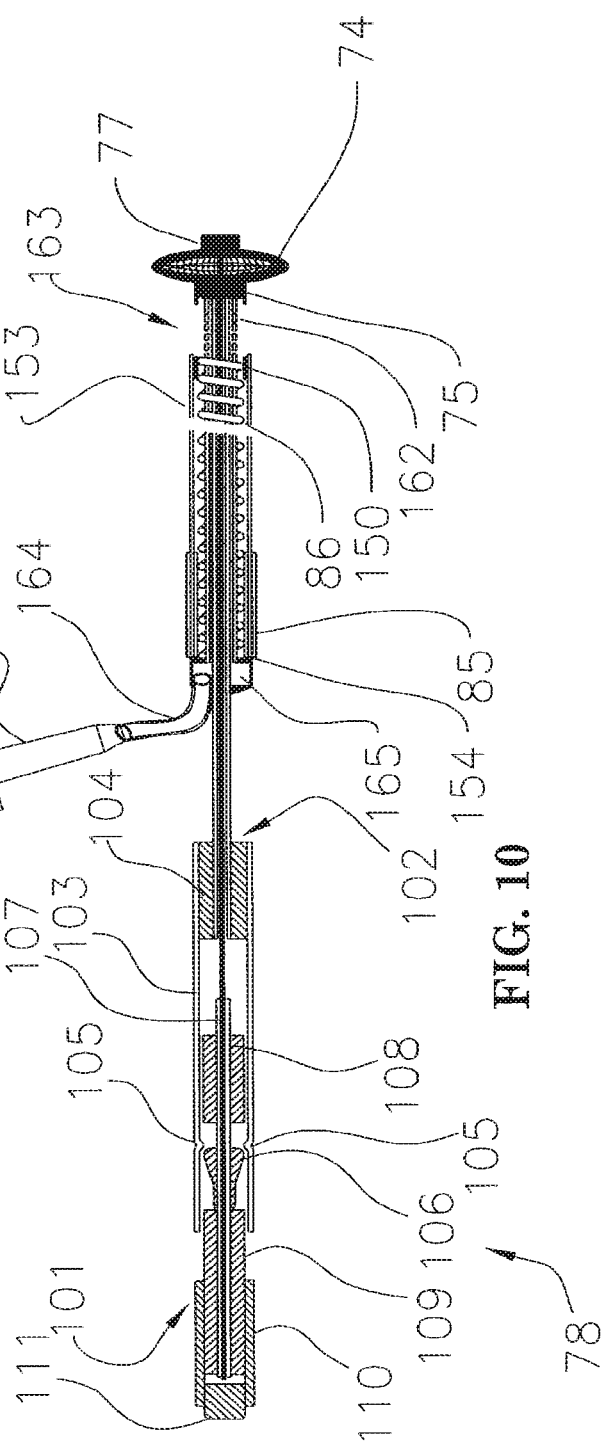

VASCULAR CLOSURE DEVICES AND METHODS PROVIDING HEMOSTATIC ENHANCEMENT

CROSS-REFERENCES TO RELATED APPLICATIONS

The present application is a continuation of U.S. patent application Ser. No. 15/424,119, filed Feb. 3, 2017, now U.S. Pat. No. 10,363,021; which is a continuation of U.S. patent application Ser. No. 14/849,228, filed Sep. 9, 2015, now U.S. Pat. No. 9,597,066; which is a continuation of U.S. patent application Ser. No. 11/772,718, filed Jul. 2, 2007, now U.S. Pat. No. 9,179,897; which is a continuation-in-part of U.S. patent application Ser. No. 11/302,951, filed Dec. 13, 2005; now U.S. Pat. No. 7,691,127; the full disclosures of which are incorporated herein by reference.

BACKGROUND OF THE INVENTION

1. Field of the Invention

The present invention relates generally to devices and methods for percutaneous sealing of puncture sites in body lumens or tissue tracts. More specifically, the present invention relates to drug eluting vascular closure devices and methods for hemostasis of vascular puncture sites.

Percutaneous access of blood vessels in the human body is routinely performed for diagnostics or interventional procedures such as coronary and peripheral angiography, angioplasty, atherectomies, placement of vascular stents, coronary retroperfusion and retroinfusion, cerebral angiograms, treatment of strokes, cerebral aneurysms, and the like. Patients undergoing these procedures are often treated with anti-coagulants such as heparin, thrombolytics, and the like, which make the closure and hemostasis process of the puncture site in the vessel wall at the completion of such interventional procedures more difficult to achieve.

Various devices have been introduced to provide hemostasis, however none have been entirely successful. Some devices utilize collagen or other biological plugs to seal the puncture site. Alternatively, sutures and/or staples have also been applied to close the puncture site. External foreign objects such as plugs, sutures, or staples however may cause tissue reaction, inflammation, and/or infection as they all "leave something behind" to achieve hemostasis.

There is also another class of devices that use the body's own natural mechanism to achieve hemostasis wherein no foreign objects are left behind. Such devices typically provide hemostasis by sealing the puncture site from the inside of the vessel wall wherein the device is left in place in the vessel lumen until hemostasis is reached and thereafter removed. Although such safe and simple devices have achieved relative levels of success, they often can be slow in achieving complete hemostasis, particularly in highly anti-coagulated patients. Of particular interest to the present invention, examples of such devices are described in co-pending, commonly owned application Ser. No. 10/795,019 filed on Mar. 3, 2004; Ser. No. 10/821,633, filed on Apr. 9, 2004; Ser. No. 10/857,177, filed on May 27, 2004; and Ser. No. 10/974,008, filed on Oct. 25, 2004, the full disclosures of which are incorporated herein by reference.

There is yet another class of devices where highly thrombogenic substances are mixed and injected to the puncture site for the purpose of accelerating the hemostatic process. These mixtures contain one or more clot promoting substances, such as thrombin and/or fibrinogen, along with other substances, such as collagen. These devices generally work by first occluding the puncture site from the inside of the vessel, usually by use of a balloon, and then injecting the mixture into the tissue tract. The balloon is then removed. Such devices suffer from several drawbacks which may cause severe complications. For example, the occluding member may not be adequate to prevent these highly thrombogenic substances from entering the blood vessel. Further, the injection of the mixture is often not well controlled and highly technique dependent, which again may allow these substances to enter the blood stream.

In light of the above, it would be desirable to provide alternative devices and methods for providing complete hemostasis of a puncture site in a body lumen, particularly blood vessels of the human body. It would be particularly desirable if such devices and methods utilize the body's own natural healing mechanism to achieve hemostasis. It would be further desirable if the natural hemostatic process can be safely accelerated by the controlled use of chemical and/or biological agents. It would be further desirable if such devices and systems utilize a simple construction and user interface allowing for convenient application without numerous intermediary steps. Further, such devices should be safe and reliable without the need for much user intervention. At least some of these objective will be met by the devices and methods of the present invention described hereinafter.

2. Description of the Background Art

Hemostasis devices for use in blood vessels and tracts in the body are described in pending U.S. patent application Ser. Nos. 10/974,008; 10/857,177; 10/821,633; 10/795,019; and 10/718,504 and U.S. Pat. Nos. 6,656,207; 6,464,712; 6,056,770; 6,056,769; 6,045,570; 6,022,361; 5,951,589; 5,922,009; and 5,782,860, assigned to the assignee of the present application. The following U.S. Patents and Publications may be relevant to the present invention: U.S. Pat. Nos. 4,744,364; 4,852,568; 4,890,612; 5,108,421; 5,171,259; 5,258,000; 5,383,896; 5,419,765; 5,454,833; 5,626,601; 5,630,833; 5,634,936; 5,728,134; 5,836,913; 5,861,003; 5,868,778; 5,951,583; 5,957,952; 6,017,359; 6,048,358; and 6,296,657; U.S. Publication Nos. 2002/0133123; 2003/0055454; 2003/0045835; and 2004/0243052. The full disclosures of each of the above mentioned references are incorporated herein by reference.

SUMMARY OF THE INVENTION

The present invention provides closure devices and methods for percutaneous access and closure of puncture sites in a body lumen, particularly femoral arteries and other blood vessels of the human body. It will be appreciated however that application of the present invention is not limited to the blood vasculature, and as such may be applied to any of the vessels, even severely tortuous vessels, ducts, and cavities found in the body as well as tissue tracts. Such closure devices and methods utilize the body's own natural healing mechanism to achieve hemostasis.

In particular, the present invention provides methods and devices for closing and sealing luminal punctures by providing physical occlusion of the puncture site together with chemical or biological promotion of hemostasis activity proximal of the occlusion. Methods for closing a blood vessel or other luminal puncture site located at a distal end of a tissue tract comprise introducing a closure device through the tissue tract. An expansible member is then deployed from the device within the blood vessel or other body lumen in order to occlude the puncture site. Blood within the vessel wall puncture and the tissue tract proximal to the puncture is exposed to a chemical and/or biological agent carried by the device. The chemical and/or biological agent is selected to promote hemostasis within the tissue tract. After sufficient hemostasis and closure has been achieved, the expansible member will be collapsed and the device removed from the tissue tract, thus eliminating or significantly reducing the need to apply external pressure to maintain hemostasis and promote healing.

In one exemplary embodiment, the chemical and/or biological agent is immobilized on the device, typically in a region immediately proximal to the expansible member, and is exposed by displacing a sealing member which initially covers the chemical and/or biological agent. Typically, the sealing member is a tubular sheath or other member which covers the chemical and/or biological agent as the device is introduced through the tissue tract and which may be axially retracted after the expansible member has been deployed within the blood vessel or other body lumen. It will be appreciated, however, that the sealing member could comprise a wide variety of other configurations, including a rotatable component, a tear-away component, a biodegradable component which dissolves upon exposure to blood or other body fluids, or the like.

The immobilized chemical and/or biological agent may be either soluble or insoluble. Soluble chemical and/or biological agents will be selected so that at least a portion thereof will dissolve and be released into the blood after the agent has been exposed to the tissue tract. Exemplary soluble chemical and/or biological agents are selected from the group consisting of thrombin (a pro-coagulant), epinephrine (a vasoconstrictor), watersoluble chitosan (a platelet aggregator), and the like.

Insoluble immobilized chemical and/or biological agents will typically have a catalytic or physical activity which promotes hemostasis. For example, the insoluble chemical and/or biological agents may have a negative electrical charge which promotes coagulation. Exemplary chemical and/or biological agents having such a negative charge include kaolin and silica. Alternatively, the insoluble chemical and/or biological agents may have a positive electrical charge which attracts platelets to promote clotting. Exemplary insoluble chemical and/or biological agents having a positive charge include chitosan. Still further, the insoluble chemical and/or biological agents may inhibit the activity of heparin in inhibitors include protamine sulfate.

Instead exposing an immobilized chemical and/or biological agent, the methods of the present invention may comprise injecting or otherwise delivering the chemical and/or biological agent into the tissue tract in the region proximal to the deployed expansible member. Such injection will typically be through an injection lumen provided within the device but could also be through a separate lumen or device. Exemplary injectable chemical and/or biological agents include thrombin, epinephrine, protamine sulfate, suspensions of insoluble kaolin, silica, or chitosan, and the like.

Devices according to the present invention will comprise a shaft having a proximal end, a distal end, and an expansible member located near the distal end on the shaft. The shaft will be configured to be advanced through the tissue tract in order to locate the expansible member through the blood vessel or other luminal puncture site so that the expansible member may be expanded within the lumen. A sealing member is retractably disposed over at least a portion of the shaft proximal to the expansible member, and a chemical and/or biological agent selected to promote hemostasis is disposed beneath the sealing member so that at least a portion of the agent may be exposed by retracing or otherwise moving the sealing member. The chemical and/or biological agents are typically immobilized on the shaft, and exemplary immobilized agents have been described above in connection with the methods of the present invention.

In a first embodiment, a device for closing a blood vessel puncture site disposed at a distal end of a tissue tract comprises a shaft having a proximal end and a distal end, an expansible member, a chemical and/or biological sealing member, and a chemical and/or biological region or release region. The shaft is configured to advance through the tissue tract while the expansible member disposed on the distal end of the shaft is deployable within the blood vessel. The chemical and/or biological sealing member is slidably disposed over the shaft and proximal the expansible member. The chemical and/or biological region or release region is disposed under the sealing member. Advantageously, displacement of the chemical and/or biological sealing member in a proximal direction exposes the region so as to allow for safe and controlled release of chemical and/or biological agents into the tissue tract for enhanced and complete hemostasis of the puncture site.

The chemical and/or biological sealing member prevents severe complications as a result of chemical and/or biological agents from coming in contact with the blood stream by only allowing for the controlled exposure of such agents in the tissue tract. The sealing member has a length in a range from about 0.1 cm to about 100 cm, typically from about 5 cm to about 20 cm and a diameter in a range from about 0.5 mm to about 5 mm, typically from about 1 mm to about 3 mm. The sealing member may be a tubular member formed from a variety of medical grade materials, including coiled stainless steel tubing or polymer materials such as nylon, polyurethane, polyimide, PEEK®, PEBAX®, and the like.

In a preferred embodiment of the device, a tensioning element, such as a spring or coil, is further provided. The tensioning element is slidably disposed over the shaft and under the sealing member proximal the expansible member. Generally, during application of the device, the tensioning element is preferably positionable in the tissue tract, but in other instances may be outside the tissue tract. The tensioning element gauges how much tension is being applied to the expansible member as it is seated against the puncture site so as to prevent a user from applying excessive force on the device causing undesirable movement (e.g., device is pulled out of patient body). The tensioning element also provides device compliance in cases of patient movement while the device is in place. The expansible member allows for sealing of the puncture site while the tensioning element along with an external clip apply and maintain tension to the expansible occluder so that it is seated against the puncture site at a vascular surface (e.g., blood vessel wall).

The tensioning member typically comprises a spring or coil of wire formed from a variety of medical grade materials including stainless steel, shape memory alloy, superelastic metal, and the like. The wire may have a diameter in a range from about 0.02 mm to about 1 mm and form any number of loops, typically from 1 to 30 loops. The spring or coil diameter will be in a range from about 1 mm to about 10 mm in a 10 relaxed state. As discussed in more detail below, the relaxed spring diameter is sufficiently large to allow it to be slidably received over the catheter body and greater than an inner diameter of an introducer sheath. A tubular member may additionally be slidably disposed over the catheter body and coupleable to a proximal end of the tensioning member. Such a tubular member may aid in loading and removal of the tensioning element as well as provide a mechanism for applying a predetermined amount or additional tension upon the expansible member.

Positioning the expansible member against the vessel wall positions the chemical and/or biological region or release region outside the vessel lumen at a predetermined distance from the vessel wall and proximal the expansible member. Therefore, the expansible member provides not only occlusion at the vessel puncture site but also functions as a locator so as to position the chemical and/or biological region or release region outside the vessel lumen. This in turn ensures safe release of chemical and/or biological agents in the tissue tract and outside the blood stream. The predetermined distance is in a range from about 0 to about 20 mm, typically in a range from about 2 mm to about 10 mm.

The chemical and/or biological region or release region has a length in a range from about 1 mm to about 100 mm, typically in a range from about 5 mm to about 70 mm. It will be appreciated that the length and/or volume of the region may be varied in order to integrate and release and/or expose the desired amount of chemical and/or biological agent. In one embodiment, the chemical and/or biological region includes at least one chemical and/or biological agent disposed on the distal end of the shaft proximal the expansible member and distal the tensioning element. In another embodiment, the region includes at least one chemical and/or biological agent disposed on the tensioning element. The agents may be coated, sprayed, molded, dipped, vapor deposited, plasma deposited, or painted thereon. Such a chemical and/or biological region on the occlusion device itself further minimizes variations due to user techniques, which may be particularly problematic with injection protocols where such agents are injected into the tract by the user. In yet another embodiment, the device may further incorporate an expansible feature disposed on the distal end of the shaft proximal the expansible member, wherein the region includes at least one chemical and/or biological agent associated with the expansible feature.

In alternative embodiments of the present invention, the device may further incorporate at least one chemical and/or biological delivery conduit disposed over the shaft and under the tensioning element and a chemical and/or biological injection port in fluid communication with the delivery conduit. The injection port may be connected to a syringe by use of a compression fitting or with an integrated luer lock. The chemical and/or biological agents are injected into the device via the syringe once the device is properly positioned. It will be appreciated that the size of the injection port and the delivery conduit may be selected to control the delivery rate of such agents. In one example, the release region includes at least one opening, aperture, or orifice in fluid communication with a distal end of the conduit proximal the expansible member. It will be appreciated that any number, size, and/or shape of opening(s) may be utilized in order to obtain the desired release rate of chemical and/or biological agent. The release region may incorporate about 1 opening to about 100 openings, typically about 1 opening to about 10 openings. In another example, the release region includes at least one porous member in fluid communication with a distal end of the conduit proximal the expansible member so as to allow for the desired release of the chemical and/or biological agent.

A controlled delivery rate allows the chemical and/or biological agents to "ooze" out of the release region. This may eliminate the potential of high pressure release, which in turn minimizes the possibility of these agents from entering the blood stream. In addition, the sealing member serves to cover the chemical and/or biological release region so as to prevent any blood from flowing back through the release region, through the delivery conduit, and out through the injection port. The sealing member is only slidably displaced, revealing the chemical and/or biological release region, when it is desirable to deliver the chemical and/or biological agents.

The device of the present invention may further incorporate a spacer element disposed between the sealing member and the tensioning element so that the sealing member may easily slide over the tensioning element. The spacer element may be a tubular member formed from a variety of materials, including tubular polymer materials such as nylon, polyurethane, polyimide, PEEK®, PEBAX®, and the like. The device further includes a handle on a proximal end of the shaft. A safety tab may be disposed between the handle and the sealing member. The safety tab prevents any undesirable displacement of the sealing member so as to inhibit inadvertent release of chemical and/or biological agents.

The present invention integrates the expansible member, chemical and/or biological sealing member, chemical and/or biological region or release region, and tensioning element in a single unitary catheter construction. This simple construction and user interface allows for safe, easy and convenient application of the device without numerous intermediary steps. The sealing member in combination with the locating expansible member ensures that the chemical and/or biological region or release region is only exposed in the tissue tract. This results in a more reliable, safe, and effective device which provides immediate and complete hemostasis, which in turn reduces the risk of bleeding, hematoma formation, thrombosis, embolization, and/or infection.

In another aspect of the present invention, methods for hemostasis of a puncture site in a blood vessel at a distal end of a tissue tract are provided. One method comprises introducing any one of the closure devices as described herein through the tissue tract. The expansible member is deployed at a distal end of the device within the blood vessel. The chemical and/or biological sealing member disposed proximal the expansible member is then displaced once properly positioned so as to expose a chemical and/or biological region or release region of the device. At least one chemical and/or biological agent is then released from and/or exposed on the device and into the tissue tract.

The sealing member is displaced in a proximal direction so as to expose at least a portion of the region. This displacement distance is in a range from about 0.1 cm to about 10 cm, typically from about 0.5 cm to about 7 cm. The method further comprises deploying the tensioning element disposed proximal the expansible member within the tissue tract so that the expansible member is seated against a puncture site. Typically, deploying the tensioning element and displacing the sealing member is carried out simultaneously so as to provide for easy and convenient application of the device without numerous intermediary steps. However, it will be appreciated that deployment of the tensioning element may be carried out independently, typically prior to displacement of the sealing member, so as to provide for proper positioning of the region or release region within the tissue tract and closure of the puncture site.

The amount of tension applied to the expansible member by the tensioning coil or spring is in the range from about 0.5 ounce to 30 ounces, typically in a range from about 2 ounces to 10 ounces. As described above, the expansible member locates and closes the puncture site in the blood vessel wall. Coil elongation is sufficient to provide adequate amount of tension on the expansible member to temporary seal the puncture and to adequately displace the sealing member to reveal the chemical and/or biological region or release region. In some embodiments, coil elongation may be limited by a coupling member. Generally the amount of elongation of the tensioning coil may be the same as for displacement of the sealing member. The tension provided by the tensioning coil and the exposure of the chemical and/or biological agents may be maintained by application of an external clip on the tensioning coil, generally over the sealing member, wherein the clip rests over the skin at the puncture site.

Chemical and/or biological agent release generally comprises positioning the region at a predetermined distance proximal to the expansible member and outside the blood vessel wall. In particular, increasing the tension in the coil positions the expansible member against the puncture site and locates the chemical and/or biological region or release region in the tissue tract at the predetermined distance. Further increase in tension will cause the sealing member to disengage from an attachment point at the proximal end of the expansible member and the tensioning coil to elongate. Elongation of the tensioning coil will result in the sealing member to slide proximally so as to expose the region to the surrounding tissue for release of the chemical and/or biological agent.

The chemical and/or biological agents may accelerate the coagulation process and promote the formation of coagulum at the puncture site so to achieve complete hemostasis. The chemical and/or biological agent may comprise a variety of agents including clot promoting agents (e.g., thrombin, fibrinogen, etc.) or vaso-constricting agents (e.g., epinephrine, etc.). The chemical and/or biological agent is released and/or exposed at least about 0.1 minute, typically from about 0.5 minute to about 4 hours, usually for the entire time that the occlusion device remains deployed. As described above, the occlusion device may be modified in several ways (e.g., region length, region volume, release region openings, conduit dimensions, number of conduits, or port dimensions) to achieve the desired chemical and/or biological agent release or exposure characteristics (e.g., rate, amount, time, etc.). The methods of the present invention may involve re-hydrating the chemical and/or biological agent with fluid in the tissue tract so as to generate coagulum. These agents may use the blood components to form a coagulum even at the presence of anti-coagulants.

As described above, the chemical and/or biological agent may be coated, sprayed, molded, painted, dipped, or deposited at the region. Alternatively, chemical and/or biological agents may be injected in a delivery conduit in fluid communication with at least one opening disposed at the release region. The sealing member in such an embodiment further prevents any blood from flowing back through the openings of the release or exposure region prior to placing the expansible member against the vessel wall when the release region is in the vessel lumen. Injection of chemical and/or biological agents in the presence of blood in the chemical and/or biological delivery pathway may cause undesirable coagulum to form in the pathway which could prevent the chemical and/or biological agents from reaching the target site.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIGS. 1A and 1B illustrate a first embodiment of a drug eluting, self-tensioning vascular closure device for hemostasis of vascular puncture sites constructed in accordance with the principles of the present invention.

FIGS. 4A and 4B illustrate the device of FIGS. 1A and 1B in an expanded configuration with the occluding member under tension after removal of the safety seal and with the chemical and/or biological sealing member displaced proximally so as to expose the contents of the chemical and/or biological region.

FIGS. 5A through 5F illustrate a method for hemostasis of a puncture site in a body lumen employing the device of FIGS. 1A and 1B.

FIG. 6 illustrates a second embodiment of a drug eluting, self-tensioning vascular closure device for hemostasis of vascular puncture sites constructed in accordance with the principles of the present invention.

FIG. 7 illustrates an exploded view of the chemical and/or biological injection port and delivery conduit of the device of FIG. 6.

FIG. 8 illustrates an exploded view of the chemical and/or biological release region on the distal end of the device of FIG. 6.

FIG. 9 illustrates the device of FIG. 6 in an expanded configuration with the occluding member deployed.

FIG. 10 illustrates the device of FIG. 6 in an expanded configuration with the occluding member under tension and with the chemical and/or biological sealing member displaced proximally so as to expose the chemical and/or biological release region so that attachment of a syringe to the chemical and/or biological injection port provides delivery of chemical and/or biological agents.

DETAILED DESCRIPTION OF THE INVENTION

Figure 2A:
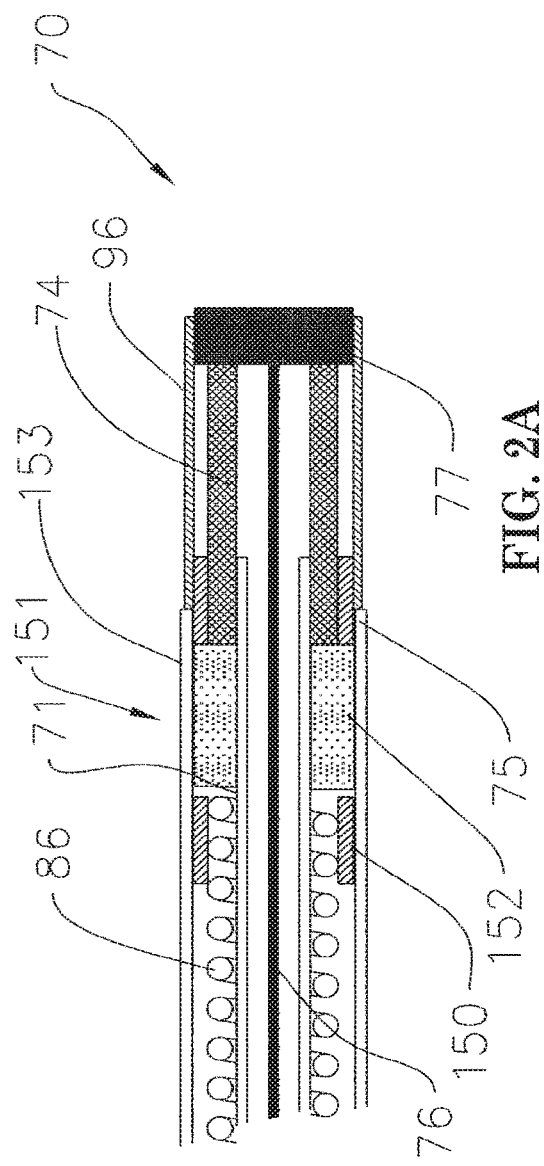
FIGS. 2A and 2B illustrate an exploded view of the chemical and/or biological region on the distal end of the device of FIGS. 1A and 1B.
Figure 2B:
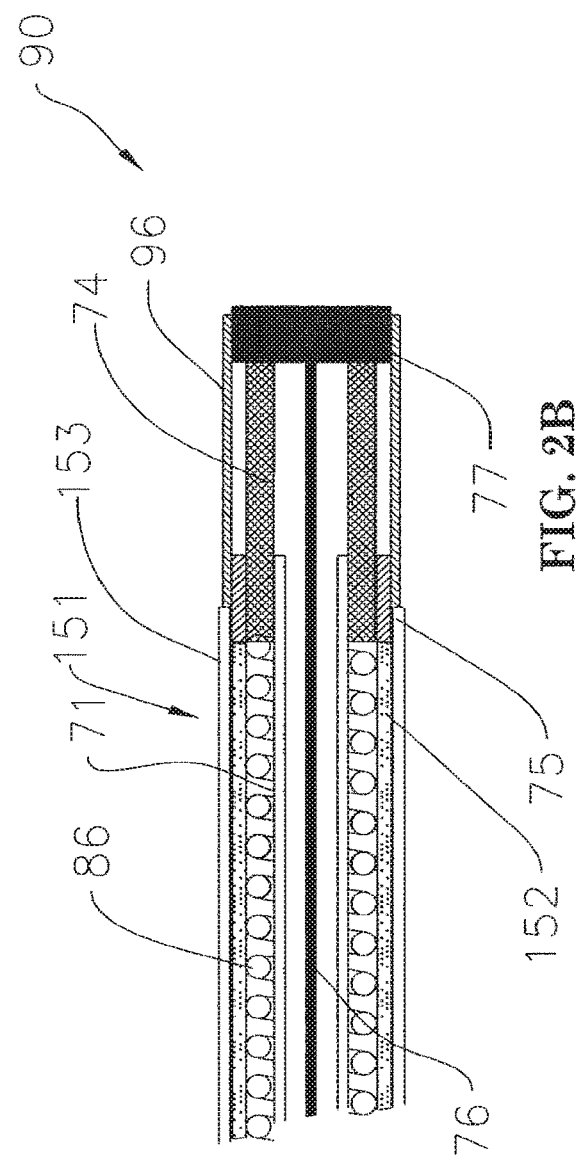

Referring now to FIGS. 1A and 1B, a first embodiment of a drug eluting, self-tensioning vascular occlusion device 70 for hemostasis of vascular puncture sites is illustrated, wherein at least one chemical and/or biological agent 152 is integrated with the device, typically being immobilized in or over a region, chamber, or absorptive reservoir 151 (referred to collectively as a chemical and/or biological region). Device 70 generally comprises a first flexible elongated tubular member 71 formed from coiled stainless steel tubing or polymer materials such as nylon, polyurethane, polyimide, PEEK®, PEBAX®, and the like. Tubular member 71 may have a length in a range from about 5 cm to about 50 cm, typically in the range from about 10 cm to about 30 cm and a diameter in the range from about 0.25 mm to about 5 mm, typically in the range from about 0.5 mm to about 2 mm. An expansible occlusion member 74 is disposed on the distal end of tubular member 71. A chemical and/or biological sealing member 153 is slidably disposed over the tubular member 71 and proximal the expansible member 74. The chemical and/or biological agent region 151 containing the chemical and/or biological agent 152 is typically disposed on the tubular member 71 (and/or optionally over a tension coil as illustrated in device 90 in FIG. 1B) under the sealing member 153. Device 70 (FIG. 1A) and device 90 (FIG. 1B) differ only in the location of the chemical and/or biological agent. It will be appreciated that the above depictions are for illustrative purposes only and do not necessarily reflect the actual shape, size, or dimensions of the device 70. This applies to all depictions hereinafter.

The expansible member 74 may be formed from a variety of medical grade materials, including stainless steel, superelastic material such as NITINOL®, or polymer materials such as nylon, polyurethane, polyimide, PEEK®, PEBAX®, and the like. Preferably the expansible member 74 is made of superelastic NITINOL® material. The expansible member 74 in a retracted or collapsed state has a diameter of less than about 3 mm, preferably less than about 1.5 mm, as shown in FIGS. 1A and 1B, and FIGS. 2A and 2B. When deployed, the expansible member 74 in an expanded state has a diameter in a range from about 3 mm to about 20 mm, preferably from about 3.5 mm to about 8 mm, as shown in FIGS. 3A/B and 4A/B. Exemplary expansible structures 74 are described in detail in co-pending U.S. patent application Ser. No. 10/718,504. Still further embodiments of a braided mesh member 74 are described in U.S. Pat. No. 5,836,913.

The expansible member 74 may at least partially or preferably be fully covered with an elastomeric membrane material 96. Membrane 96 may be formed from a variety of medical grade materials, such as thermoplastic elastomers (e.g., CHRONOPRENE® or POLYBLEND®) having durometers in a range from 15 A to about 40 A. Membrane 96 may be connected at a distal connection point 77 and a proximal connection point 75. Adhesives such as LOC-TITE® 4014 may be used to attach membrane 96 to the expansible member 74 and catheter shaft 71. Alternatively, membrane 96 may take a form of a sock having its distal end sealed through a heat stake process or the like. In this case membrane 96 may not have to be attached distally. Membrane 96 preferably has a diameter that is sufficient to cover the expansible member 74. In some embodiments, membrane 96 may be designed and attached to facilitate expansible member deployment as well as to reduce the amount of required elongation when the expansible member 74 is deployed. This may be achieved by molding the membrane 96 so that its midpoint diameter, where deployed expansible member 74 has its greatest diameter, is larger than its proximal and distal end diameters (e.g., a spherical shape). Membrane 96 may also be formed like a tube with a larger diameter than needed (e.g., diameter of retracted expansible member 74), and then stretched over expansible member 74 and attached. The stretch should be enough to reduce the diameter of the membrane 96 to that of the expansible member 74. In such a case, when member 74 is deployed, there is less elongation and stress experienced by membrane 96. The membrane 96 may additionally form a membrane tip at a distal end of catheter 70 so as to provide a soft and blunt point for safer percutaneous access.

Figure 3A:
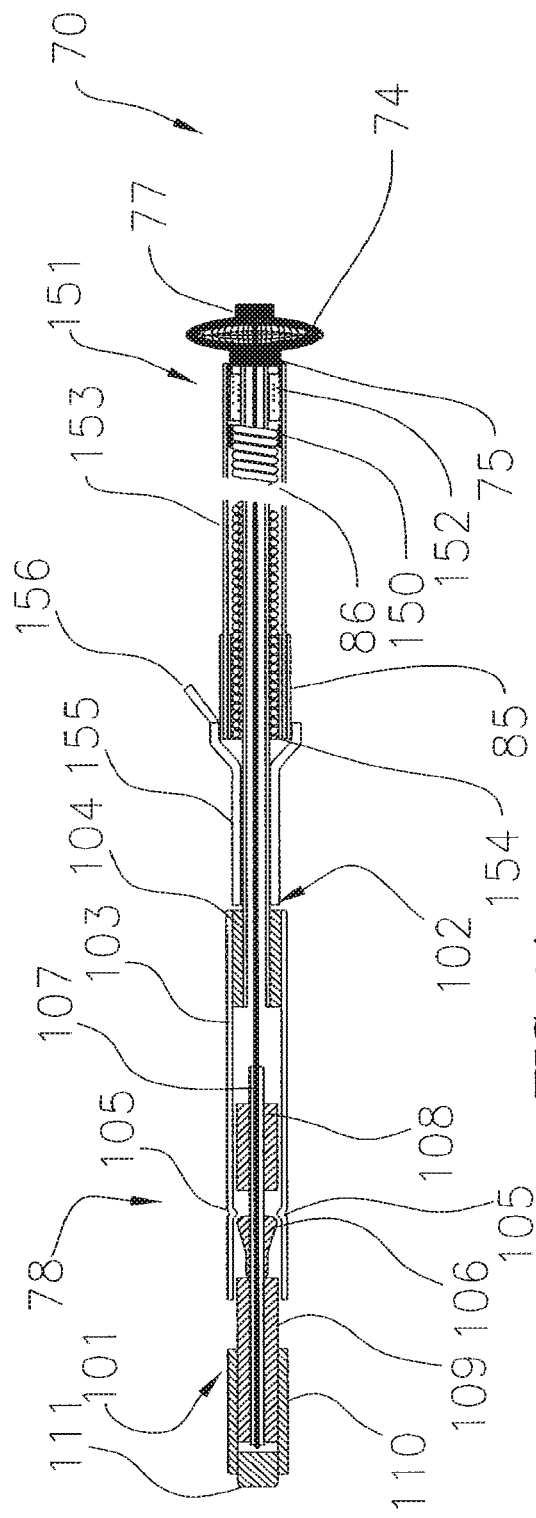
FIGS. 3A and 3B illustrate the device of FIGS. 1A and 1B in an expanded configuration with the occluding member deployed.
Figure 3B:
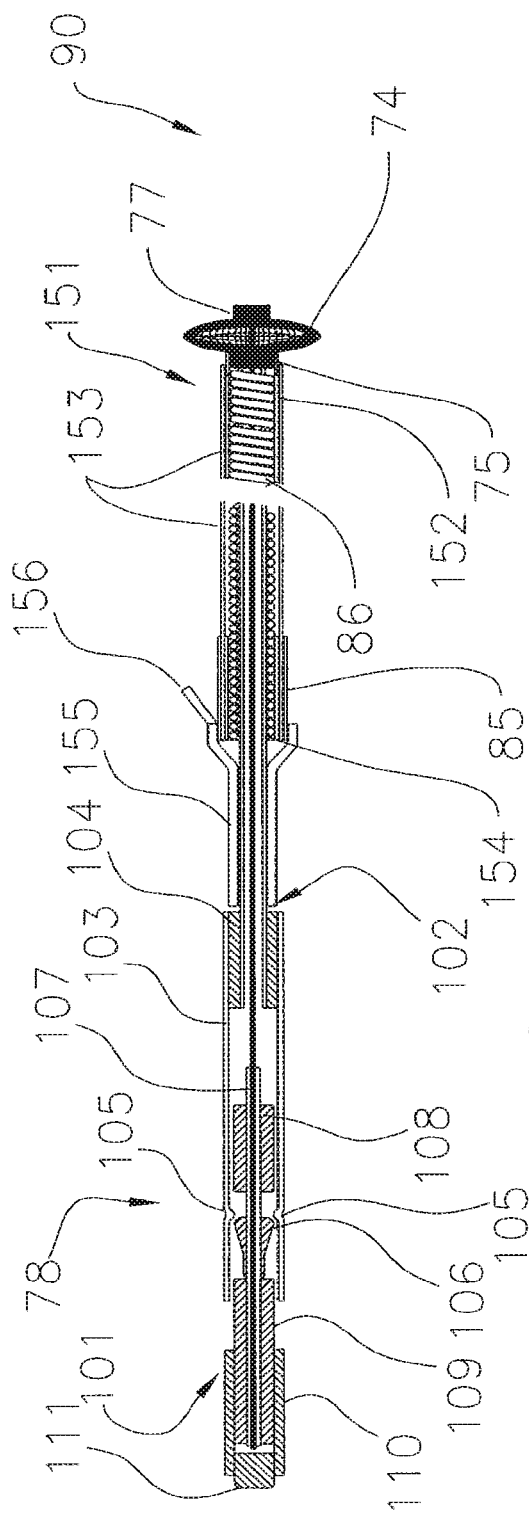

Referring now to FIGS. 2A/B, the chemical and/or biological agents 152 may be composed of clot promoting agents such as thrombin and fibrinogen and/or vaso-constrictors such as epinephrine. These agents 152 may take on a form of a powder, paste that can be applied to the chemical and/or biological chamber or region 151. Alternatively, such agents 152 may be molded in a form of a cylindrical tube with a longitudinal central hole that can be slidably disposed over member 71 and positioned between fixed attachment members 75 and 150 in the assembly process. The chemical and/or biological chamber/region 151 is located between the proximal end of member 75 and distal end of attachment member 150. Alternatively, or additionally, the chemical and/or biological agents may be immobilized on the tension coil 86 described below. The length of region 151 determines the amount of chemical and/or biological agents 152 that can be integrated with the device, as well as the extent of the exposure of such agents to the tissue. It should also be noted that by increasing the outside diameters of members 75 and 150, the volume of chamber 151 can be increased and hence the volume of the chemical and/or biological agents 152 incorporated with the device. However, it may be desirable to allow for a predetermined volume of blood to enter the gap between the chemical and/or biological agent layer and the sealing member 153. This allows exposure of the chemical and/or biological agents to the bodily fluids without exposing these agents to the body. The trapped blood can then be given sufficient amount of time to interact with the agents to become preconditioned prior to exposure to tissue tract. The volume of this trapped blood may be controlled by adjusting the gap between the chemical and/or biological layer and the inside diameter of the sealing member. The degree of preconditioning may be controlled by selecting the amount of time between the insertion of the device in the sheath and exposure of the agent(s) to blood and when the tension is applied and the sealing member is proximally displaced. The gap fills quickly due to capillary pull and the arterial blood pressure once the distal end of the sealing member 153 comes in contact with blood.

The chemical and/or biological sealing member 153 generally comprises a flexible elongated tubular member. In the device 70 of FIG. 1A, the tubular member 153 may have a length that extends from attachment member 75, and overlapping member 75, to grip member 85, partially or fully overlapping member 85. The inside diameter of member 153, at least at the distal end, is similar to the outside diameter of member 75. Member 153 is slidably positioned, at least partially, over member 75. The interaction of members 153 and 75 provide for a barrier so that blood will not come in contact with the chemical and/or biological agent prior to the intended time.

In the preferred embodiment of the present invention, a tensioning element 86 is slidably disposed over the tubular member 71 and proximal the expansible member 74. The tensioning coil 86 is attached to the tubular member 71 with attachment member 150. Member 150 may be in a tubular form and made from stainless steel tubing or polymer materials such as nylon, polyurethane, polyimide, PEEK®, PEBAX®, and the like. Coil 86, attachment member 150 and tubular member 71 are connected together by use of epoxy. The attachment point may be from 1 mm to 100 mm proximal to the member 75, preferably in the range of 5 mm to 50 mm. The tensioning element 86 is described in more detail in co-pending U.S. patent application Ser. No. 10/974,008.

The function of chemical and/or biological seal 153 is to provide a barrier between the chemical and/or biological agents 152 and bodily fluids such as blood, and only allow the exposure of such agents to the tissue when the device is in correct position and the operator chooses to do so. Exposure of the chemical and/or biological region 151 to the surrounding tissue happens when the tensioning coil 86 is grabbed at grip member 85 and is pulled proximally with respect to member 75 to apply tension to the deployed expansible member 74 at the puncture site. The proximal pull of grip member 85 causes the tensioning coil 86 to elongate. The seal member 153 is attached to the coil 86 and grip member 85. Since member 153 is not stretchable, the elongation of coil 86 results in disengagement of the distal end of member 153 from member 75. Seal 153 slides proximally over the chemical and/or biological chamber/region 151 and exposes the chemical and/or biological agents 152 to the surrounding tissue. A spacer 154 provides adequate space between coil 86 and sealing member 153, so that member 153 can easily slide over coil 86. It should be noted that coil 86 elongation happens as the result of interference of the occluding expansible member 74 with the vessel wall at the puncture site. This in turn slides the sealing member 153 proximally, exposing the chemical and/or biological agents 152 in the tissue tract where it is needed.

It will be appreciated that chemical and/or biological seal 153 may be constructed to function independently from the tensioning coil 86. Also, in some embodiments, such as those of FIGS. 1B, 2B, 3B and 4B, a length of coil 86, or the entire length of coil 86 may be coated with the chemical and/or biological agent 152. In such case, when coil spring 86 is elongated to provide tension to the expansible member 74, the deformation of the elongating coil spring 86 may result in breaking off of the agents 152 from the coil. This may result in faster re-hydration of the chemical and/or biological agents 152 and consequently acceleration of the coagulation process in the tract. Coating of the coil 86 is not limited to such brittle agents, however, and the agents may be sufficiently "flexible" so that they remain immobilized despite stretching of the coil. Still further, the chemical and/or biological chamber 151 of device 70 may include an expansible feature over which the chemical and/or biological agent 152 is dispensed (e.g., coated). When desirable, this expansible member which may take the form of a balloon or a braided mesh, can be expanded, resulting in the agents 152 breaking off in the surrounding tissue, and hence accelerating the chemical and/or biological reaction.

The device 70 of the present invention may further incorporate a safety seal 155 to prevent inadvertent release of chemical and/or biological agents 152 by preventing coil 86 from sliding over member 71. Safety seal 155 may be made of different materials and be implemented in different fashions. One such implementation may take the form of heat shrinkable tubing. The tubing may be shrunk over member 71 to the proximal end of the coil 86 or preferably overlapping grip member 85. To remove the safety seal with ease, seal 155 may have a tab 156 that may be easily grabbed and pulled, tearing the safety seal 155 along the length of member 71. Removal of the safety seal 155 would allow coil 86 to freely slide over tubular member 71, exposing the chemical and/or biological agents 152 to the surrounding tissue.

The chemical and/or biological agent 152 is sealed from coming in contact with the circulating blood and generally is released and/or exposed in the tissue tract in the fascia at the puncture site. During device application, the expansible member 74 will be positioned and anchored against the puncture site in the vessel lumen. In particular, the expansible member 74 allows for sealing of the puncture site and locating the chemical and/or biological agents 152 appropriately in the tissue tract. The tensioning element 86 applies and maintains tension to the expansible occluder 74 while the sealing member 153 simultaneously reveals the chemical and/or biological agents 152 to bring such agents in contact with the surrounding tissue to accelerate the process of hemostasis.

Referring now to FIGS. 3A and 4A, a proximal end of the device 70 comprises deployment means 78. Deployment of the expansible member 74 typically comprises pushing or pulling the two part handle assembly 78 coupled to the expansible member 74. A proximal end of handle assembly 78 comprises an actuating assembly 101 which is coupled to a push/pull member 76. Proximal movement of assembly 101 relative to a grip handle 102 deploys the expansible member 74. The grip handle 102 comprises a tubular member 103 formed from suitable metal tubing (e.g., stainless steel) or polymer materials (e.g., polyurethane, polyimide, PEEK®, PEBAX®, and the like). Member 103 is coupled to the catheter shaft 71 by means of an expander element 104 so as to account for the difference in an outside diameter of catheter 71 and an inside diameter of member 103. Elements 71, 103, and 104 may be attached by the use of adhesives. Member 103 further includes a feature 105, such as an indentation from a crimping process when element 103 is formed from a stainless steel or other metallic hypotube. Indentation 105 provides interference to element 106 of the actuating assembly 101.

Actuating assembly 101 further includes a tubular member 107 that is attached to the push/pull member 76 by a crimp process and/or adhesive. Member 107 provides added stiffness to the actuating mechanism 101 as well as provides for a larger surface area that consequently allows for enhanced adhesion of elements 106, 108, and 109 to member 107. These elements may comprise individual, separate parts, preferably formed from polymer materials such as polyurethane, polyimide, PEEK®, PEBAX®, and the like. These elements may be optionally incorporated into element 107 through an over molding process. Once the device 70 is deployed, interference of detent element 106 with indentation 105 securely maintains the expansible member 74 in its deployed position as shown in FIGS. 3A/B and 4A/B. A proximal end of detent 106 may have a shallow angle in relation to the catheter shaft 71 so as to provide simplified deployment of the expansible member 74. A distal end of detent 106 may be more perpendicular to the catheter shaft 71 so as to provide more interference to feature 105, thereby requiring greater force to undeploy the expansible member 74. The increased undeployment force is desirable to avoid inadvertent device collapse. Optionally, indentation 105 may be designed so that a distal side of the feature has a much shallower angle in relation to the catheter shaft 71 than a proximal side.

Elements 108 and 109 primarily provide support and alignment of the actuating assembly 101. Element 109 may be formed from a bright distinct color to indicate when the expansible member 74 is deployed. Element 110 comprises a tubular member, preferably having the same outer diameter as member 103. A distal end of tubular member 110 abuts a proximal end of member 103 so as to provide a positive stop to the movement of the actuating assembly 101 during the undeployment of the expansible member 74. Cap 111 at the most proximal end of the device 70 provides a soft tip for easier undeployment of expansible member 74. Cap 111 may be formed from rubber or similar materials.

In operation, handle assembly 78 is held by grabbing onto element 103 with one hand and element 110 with the other hand. Element 110 is then pulled in a proximal direction while holding element 103 stationary. As element 110 is pulled back, detent 106 slides over indentation 105 until it is completely moved to the proximal side of feature 105. FIGS. 3A/B and 4A/B illustrate the expansible member 74 that is in the form of a tubular braided mesh in the deployed and expanded state. The interference between elements 105 and 106 keeps the expansible member 74 in the deployed configuration. Undeployment of the device 70 may be effected with a single hand. In particular, member 103 may be grabbed by the palm of the hand while the thumb presses on cap 111. This causes the actuating mechanism 101 to move forward and the detent member 106 to slide distally over feature 105 resulting in the retraction of the expansible member 74.

Figures 5C, 5D:
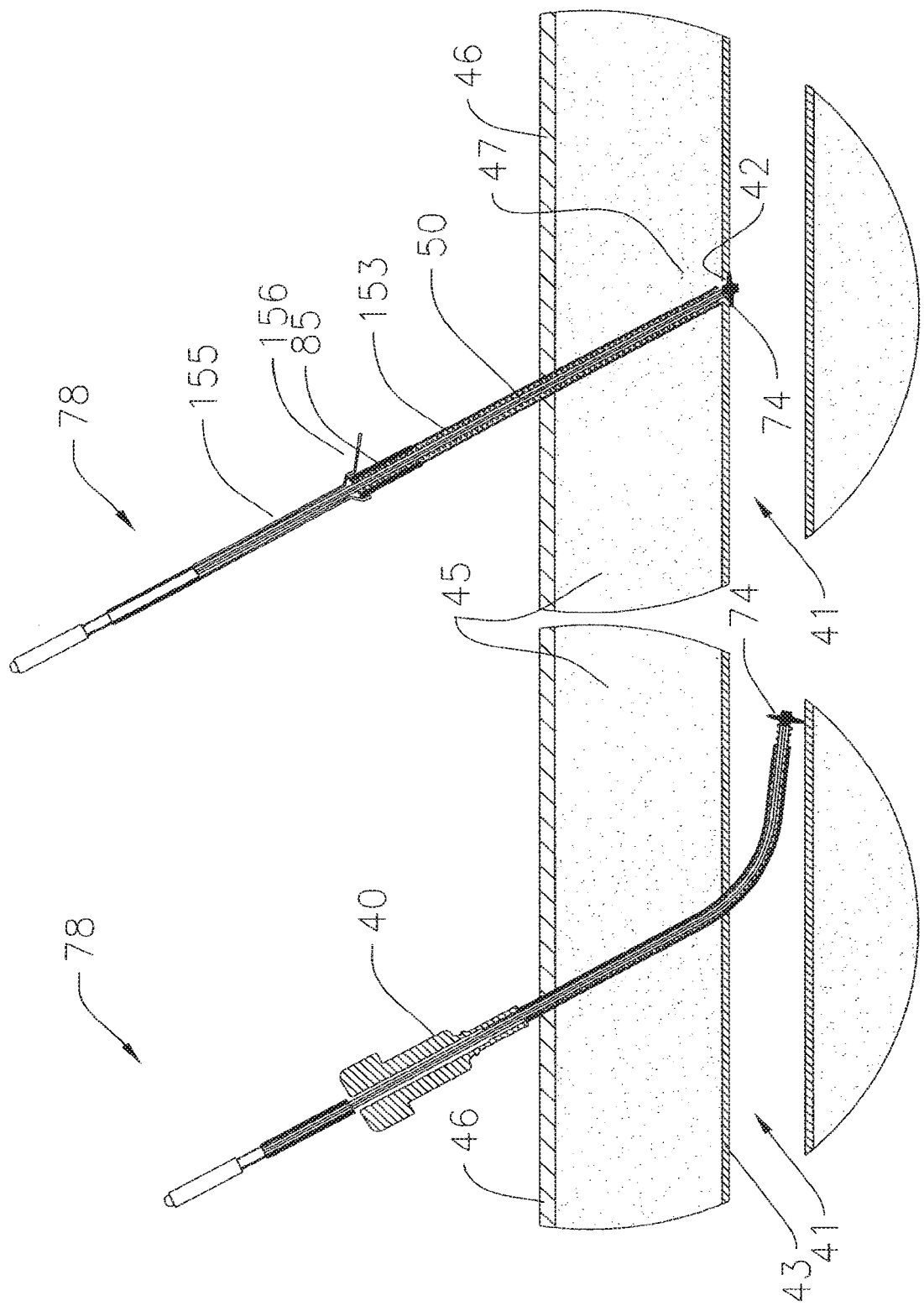

Referring now to FIGS. 5A through 5F, a method for hemostasis of a puncture site in a body lumen employing the device 70 of FIGS. 1A/B is illustrated. FIG. 5A depicts an existing introducer sheath 40 advanced through an opening in a skin surface 46, tissue tract in fascia 45 and vessel wall 43 and seated in a vessel lumen 41 at the completion of a catheterization procedure. Device 70 is then inserted through the hub of the sheath 40 and is advanced until the expansible member 74 is outside the sheath 40 and in the vessel lumen 41, as shown in FIG. 5B. This positioning may be indicated by a mark or feature on the catheter 71 or the handle assembly 78.

As shown in FIG. 5C, the expansible member 74 is then deployed by operation of the handle assembly 78. The sheath 40 is then slowly pulled out of the body, placing the expansible member 74 against the inner wall of the vessel 43 at the puncture site 42. As the sheath 40 is removed, the grip member 85 which is slidably disposed over the catheter shaft 71 and the handle assembly 78 are revealed. Sheath 40 is then discarded, leaving deployed expansible member 74 seated at the puncture site 42 and the chemical and/or biological chamber/region 151 in the tissue tract 47 as shown in FIG. 5D. If the device is equipped with the safety seal 155 as in device 70, then the safety seal 155 is removed by pulling the tab 156 proximally along the catheter shaft.

Referring now to FIG. 5E, once safety seal 155 is removed, the grip element 85 is grabbed and pulled in a proximal direction. Grip 85 is moved proximally to provide adequate amount of tension to the deployed expansible member 74 to achieve hemostasis. Typically, the amount of tension applied to the expansible member 74 is in the range of 0.5 ounces to 30 ounces. In particular, proximal movement of grip 85 causes simultaneous elongation of the tensioning coil 86, causing the expansible member to locate and close the puncture site 42, and displacement of the chemical and/or biological seal 153, exposing the chemical and/or biological agent 152 to the surrounding tissue at a predetermined distance from the puncture site. The elongated position of coil 86 is maintained by application of a small external clip 50 to the catheter and seated against the surface of the skin 46, as shown in FIG. 5E. Device 70 is left in this position for a period of time to achieve the desired promotion of hemostasis, for example to allow the chemical and/or biological agent 152 to reconstitute with the fluids in the tissue tract 47, generating coagulum, or to allow contact activation, electrostatic interaction, or the like. Clip 50 is then removed and the expansible member 74 is collapsed by manipulation of the handle assembly 78. Device 70 is then removed, leaving the active chemical and/or biological agents 152 and the coagulum in the tract 47 and adjacent the vessel puncture site 42, as shown in FIG. 5F. Additional finger pressure at the puncture site may be required to allow the coagulum to seal the small hole left in the vessel wall after removal of the device.

Referring now to FIG. 6, another embodiment of an exemplary drug eluting, self-tensioning vascular occlusion device 80 for hemostasis of vascular puncture sites is illustrated, wherein the bio-active agents 152 may be stored separately and safely injected into the target site through a chemical and/or biological release region 163 once the device is properly positioned. The chemical and/or biological delivery system of device 80 is composed of an elongated tubular member 160. Member 160 may be coaxially located over member 71 as shown in FIG. 6. 160 has an inside diameter that is larger than the outside diameter of member 71. Member 160 is formed from coiled stainless steel tubing or polymer materials such as nylon, polyurethane, polyimide, PEEK®, PEBAX®, and the like. The gap made between the inside of member 160 and the outside of member 71 defines the chemical and/or biological delivery conduit 161.

Referring now to FIG. 8, the distal end of member 160 has a plurality of openings 162 defining the chemical and/or biological release region 163. Openings 162 vary in number and may be from 1 opening to 100 opening, preferably from 1 opening to 10 openings. The size, shape, and/or number of openings 162 determines the rate of the release of the chemical and/or biological agents into the surrounding tissues. Alternatively, the chemical and/or biological release region 163 may not be part of member 160, and may be a separate member, made of porous material which is in fluid communication with member 160. In either embodiment, release region 163 is located at a predetermined distance proximal to the expansible member 74.

Referring now to FIG. 7, a chemical and/or biological injection port 164 is illustrated. Port 164 comprises a flexible elongated tubular member that transitions to member 160 at its distal end by means of a coupling member 165. At a proximal end, the port 164 provides a coupling to a syringe 167 for the injection of chemical and/or biological agents 152. Members 164 and 165 may be constructed from stainless steel tubing or polymer materials such as nylon, polyurethane, polyimide, PEEK®, PEBAX®, and the like. Member 165 may or may not be a flexible member. Member 165 preferably has an outside diameter that is not larger than the outside diameter of the handle assembly 78. This ensures that device 80 can go through the existing sheath 40 without interference, as was described for device 70 in FIGS. 5A through 5F. Coupling member 165 is connected to member 160 via member 166. Members 164, 165 and 160 are attached by means of epoxy to provide a fluid tight seal at attachment points 166.

It will be appreciated that the drug delivery conduit 160 may comprise a single or multiple elongated tubular member (s) of varying length(s) that run(s) along the length of member 71. At a proximal end, these conduits couple into delivery port 164 via coupling member 165. At a distal end, these tubular members may terminate at different points proximal to the expansible member 74, dispersed over release region 163. Distally, these conduits may have at least one opening for the release of the chemical and/or biological agents into the region.

The chemical and/or biological sealing member 153 of device 80 functions in a similar fashion as in device 70. In addition, the sealing member 153 of device 80 prevents blood from flowing back through the chemical and/or biological deliver path 163, 162, 161, 164. However, it will be appreciated that the back flow of blood through the chemical and/or biological delivery pathway may be used as an indicator that the chemical and/or biological release region 163 is in the vessel lumen. When the back flow stops, that may be an indication that the release region 163 is in the tissue tract, where there is no appreciable blood pressure. In addition to the expansible member 74, this feature may add more certainty to the positioning of the chemical and/or biological release region 163 and hence improve safety. In such case, prior to injection of the chemical and/or biological agents 152, the pathway may be flushed with solutions such as saline.

The tensioning coil 86, spacer element 154, and grip member 85 of device 80 function in a similar fashion as in device 70. In device 80, however, the elongation of tensioning coil 86 is limited by the distal end of coupling member 165 at attachment point 166. The distance between the proximal end of the coil spring 86 and the distal end of coupling member 165 at point 166 is long enough to provide the adequate amount of tension. This distance is also sufficient to allow the chemical and/or biological seal 153 to move proximally to expose the entire chemical and/or biological release region 163. FIG. 9 illustrates device 80 with a deployed expansible member 74. FIG. 10 illustrates device 80 when the coil 86 is elongated to apply adequate amount of tension to expansible member 74 and to expose the chemical and/or biological release region 163. The attachment of syringe 167 to delivery port 164 for delivery of chemical and/or biological agents 152 to the target site is also illustrated.

In operation, device 80 is inserted through the sheath 40 and advanced until the expansible member 74 is out of the sheath 40 and in the blood vessel 41. The expansible member 74 is deployed by manipulation of the handle assembly 78, the sheath 40 is removed and discarded, and the deployed expansible member 74 is placed against the inside wall of the vessel at the puncture site 42. Tension is then applied by proximally sliding grip member 85 of coil 86. The applied tension at the deployed expansible member 74 will provide hemostasis, and locates chemical and/or biological release region 163. Elongation of the coil 86 reveals the chemical and/or biological release region 163 to the surrounding tissue tract 47. The tension and coil elongation are maintained by application of an external clip 50. Syringe 167 containing the chemical and/or biological agents 152 is then connected to the chemical and/or biological injection port 164. An adequate amount of the agent(s) is injected into the site at tissue tract 47. The chemical and/or biological agents 152 promote and accelerate the hemostatic process. After injection of the chemical and/or biological agents 152, enough time is given for the agents to react with the blood tissue to form coagulum. External clip 50 is then removed, expansible member 74 is collapsed, and device 80 is removed. Removal of the device 80 may be followed by a few minutes of manual compression at the site to close the small hole left in the vessel wall.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A device for closing a blood vessel puncture site disposed at a distal end of a tissue tract, the device comprising:
   a shaft having a proximal end and a distal end, the shaft being configured to advance through the tissue tract;
   an expansible member disposed on the distal end of the shaft and being deployable within the blood vessel;
   a tensioning element slidably disposed over the shaft and proximal the expansible member, wherein the tensioning element is configured to apply tension to the expansible member when deployed and seated against the blood vessel puncture site;
   a sealing member slidably disposed over the shaft and positioned proximal to the expansible member; and
   a chemical and/or biological agent release region under the sealing member, the chemical and/or biological agent release region comprising an immobilized chemical and/or biological agent disposed on the distal end of the shaft proximal to the expansible member and distal to the tensioning element.

2. The device of claim 1, wherein the tensioning element is configured to lengthen as the tensioning element applies greater tension to the expansible member.

3. The device of claim 2, a maximum allowed tension is determined by a maximum allowed elongation of the tensioning element.

4. The device of claim 1, wherein the tensioning element comprises a coil or a spring.

5. The device of claim 1, wherein the tensioning element is configured to apply tension to the expansible member in a range from about 0.5 ounce to 30 ounces.

6. The device of claim 1, wherein the tensioning element is slidably disposed over the shaft and under the sealing member proximal the expansible member.

* * * * *